US006747141B2

(12) United States Patent
Brentano et al.

(10) Patent No.: US 6,747,141 B2
(45) Date of Patent: Jun. 8, 2004

(54) METHODS AND COMPOSITIONS FOR DETECTION OF MYCOBACTERIUM AVIUM COMPLEX SPECIES

(75) Inventors: Steven T. Brentano, Santee, CA (US); Roger L. Lankford, Coquitlam (CA)

(73) Assignee: Gen-Probe Incorporated, San Diego, CA (US)

( * ) Notice: Subject to any disclaimer, the term of this patent is extended or adjusted under 35 U.S.C. 154(b) by 63 days.

(21) Appl. No.: 09/738,972

(22) Filed: Dec. 15, 2000

(65) Prior Publication Data

US 2002/0012918 A1 Jan. 31, 2002

Related U.S. Application Data

(60) Provisional application No. 60/171,202, filed on Dec. 15, 1999.

(51) Int. Cl.[7] ............ C12Q 1/68; C12P 19/34; C07H 21/02; C07H 21/04
(52) U.S. Cl. .......... 536/24.32; 435/6; 435/91.2; 536/23.1; 536/243
(58) Field of Search ............ 435/6, 91.2; 536/24.32

(56) References Cited

U.S. PATENT DOCUMENTS

| | | | |
|---|---|---|---|
| 5,554,516 A | 9/1996 | Kacian et al. | 435/91.21 |
| 5,726,021 A | 3/1998 | Britschgi et al. | |
| 5,766,849 A | 6/1998 | McDonough et al. | 435/6 |
| 5,851,763 A | 12/1998 | Heym et al. | 435/6 |
| 5,906,917 A | 5/1999 | Hammond | 435/6 |
| 5,908,744 A | 6/1999 | McAllister et al. | 435/6 |
| 5,925,518 A | * 7/1999 | Earle et al. | 435/6 |
| 5,985,569 A | * 11/1999 | Foxall et al. | 435/6 |
| 6,136,529 A | * 10/2000 | Hammond | 435/6 |

FOREIGN PATENT DOCUMENTS

| | | |
|---|---|---|
| EP | 0395292 | 10/1990 |
| EP | 0528306 | 2/1993 |
| EP | 0792937 A2 | 9/1997 |
| EP | 0818465 | 1/1998 |
| EP | 0866071 | 9/1998 |
| EP | 0887425 A2 | 12/1998 |
| WO | WO 9416108 A1 | 7/1994 |
| WO | WO 9506755 A1 | 3/1995 |
| WO | 9534574 | 12/1995 |
| WO | 9636733 | 11/1996 |
| WO | 9723618 | 7/1997 |
| WO | 9815648 | 4/1998 |
| WO | 9850583 | 11/1998 |
| WO | WO 99/35284 | * 7/1999 |
| WO | WO 9935284 A1 | 7/1999 |
| WO | WO 0144510 A2 | 6/2001 |

OTHER PUBLICATIONS

Gingeras TR et al. simultaneous genotyping and species identification using hybridization pattern recognition analysis of generic mycobacterium DNA arrays. Genome Res., 8(5): 435–448, 1998.*

Gingeras et al. Simultaneous genotyping and species identification using hybridization pattern recognition analysis of generic mycobacterium DNA arrays. Genome Research, vol. 8: 435–448, 1998.*

Stratagene Catalog. Gene Characterization kits. Statagene Catalog. P. 39, 1988.*

Gingeras et al. Simultaneous genotyping and species identification using hybridization pattern recognition analysis of generic mycobacterium DNA arrays. Genome Res., vol. 8(5), pp 435–448, 1998.*

Kirschner et al., Genotypic Identification and Detection of Mycobacteria—Facing Novel and Uncultured Pathogens, *Diagnostic Molecular Biology—Principles and Applications*, Pershing et al., Eds., Pt. II, Sect. 1.1, pp. 173–190 (1993).

Kox et al., "Microwell Hybridization Assay for Detection of PCR Products from *Mycobacterium tuberculosis* Complex and the Recombinant *Mycobacterium smegmatis* Strain 1008 Used as an Internal Control", *J. Clin. Microbiol.*, *34*(9):2117–2120 (1996).

Suzuki et al., "Complete Nucleotide Sequence of the 16s rRNA gene of *Mycobacterium bovis* BCG", *J. Bacteriol*, *170*:2886–2889 (1988)—Abstract—1 pg.

Troesch et al., "Mycobacterium Species Identification and Rifampin Resistance Testing with High–Density DNA Probe Arrays", *J. Clin. Microbiol.*, 37(1):49–55 (1999).

Aleixo et al., "Detection of mycobacteria by shift mobility assay", retrieved from NAGENESEQ database, Sep. 28, 1999, XP–002177849.

Britschgi et al., "Rapid and sensitive detection of antibiotic-resistant mycobacteria using oligonucleotide probes specific for ribosomal RNA precursors", retrieved from EMBL database, Dec. 2, 1998, XP–002177848.

Hammond, "Helper probe for detecting a *Mycobacterium avium* complex", retrieved from NAGENESEQ database, Oct. 4, 1995, XP–002177847.

Kulski et al., "Use of a Multiplex PCR To Detect and Identify *Mycobacterium avium* and *M. intracellulare* in Blood Culture Fluids of AIDS Patients", Journal of Clinical Microbiology, Mar. 1995, pp. 668–674, vol. 33, No. 3, American Society for Microbiology, USA.

Rogall et al., "Towards a Phylogeny and Definition of Species at the Molecular Level within the Genus Mycobacterium", International Journal of Systematic Bacteriology, Oct. 1990, pp. 323–330, vol. 40, No. 4, International Union of Microbiological Societies, USA.

(List continued on next page.)

*Primary Examiner*—Jeffrey Fredman
(74) *Attorney, Agent, or Firm*—Christine A. Gritzmacher

(57) ABSTRACT

Methods of detecting *Mycobacterium avium* complex (MAC) organisms using in vitro nucleic acid amplification with amplification oligonucleotides specific for 16S rRNA or DNA sequences encoding 16S rRNA from MAC species are disclosed. Compositions and kits containing oligonucleotides for amplifying and detecting 16S rRNA or DNA sequences encoding 16S rRNA from MAC species are disclosed.

12 Claims, No Drawings

OTHER PUBLICATIONS

Ford et al., "Evaluation of the SNAP® System for the Rapid Identification of Clinically Significant Mycobacterial Species", American Society of Microbiology 1990 Annual Meeting, May 14, 1990, Abstract U–36.

Huang et al., "Nonradioactive DNA Probe for the Rapid Identification of *Mycobacterium avium* Complex from Clinical Isolates", American Society for Microbiology 1990 Annual Meeting, May 14, 1990, Abstract U–10.

Kuritza et al., "Evaluation of Nonradioactive DNA Probes for *Mycobacterium avium* Complex and *Mycobacterium tuberculosis* Complex in a Clinical Study", American Society of Microbiology 1990 Annual Meeting, May 14, 1990, Abstract U–5.

Lauderdale et al., "Bactec® 460 in Conjunction with SNAP® DNA Probes for Rapid Identification of *Mycobacterium tuberculosis* and *Mycobacterium avium* Complex", American Society of Microbiology 1990 Annual Meeting, May 14, 1990, Abstract U–27.

Lin et al., "DNA Probes Identify Three Distinct Clusters Within the *Mycobacterium avium* Complex", American Society of Microbiology 1990 Annual Meeting, May 14, 1990, Abstract U–12.

Lin et al., "DNA Probes Identify Three Distinct Clusters Within the *Mycobacterium avium* 1 Complex", American Society of Microbiology 1990 Annual Meeting, May 14, 1990, Paper No. U–12.

\* cited by examiner

SEQUENCE LISTING

```
<160> NUMBER OF SEQ ID NOS:  18

<210> SEQ ID NO 1
<211> LENGTH: 59
<212> TYPE: DNA
<213> ORGANISM: Artificial Sequence
<220> FEATURE:
<223> OTHER INFORMATION: Description of Artificial Sequence: synthetic
      promoter-primer
<221> NAME/KEY: promoter
<222> LOCATION: (1)..(33)

<400> SEQUENCE: 1
gaaattaata cgactcacta tagggagacc acacccgtag gagtctgggc cgtatctca         59

<210> SEQ ID NO 2
<211> LENGTH: 61
<212> TYPE: DNA
<213> ORGANISM: Artificial Sequence
<220> FEATURE:
<223> OTHER INFORMATION: Description of Artificial Sequence: synthetic
      promoter-primer
<221> NAME/KEY: promoter
<222> LOCATION: (1)..(33)

<400> SEQUENCE: 2
gaaattaata cgactcacta tagggagacc acatgcctcc cgtaggagtc tgggccgtat        60
c                                                                       61

<210> SEQ ID NO 3
<211> LENGTH: 57
<212> TYPE: DNA
<213> ORGANISM: Artificial Sequence
<220> FEATURE:
<223> OTHER INFORMATION: Description of Artificial Sequence: synthetic
      promoter-primer
<221> NAME/KEY: promoter
<222> LOCATION: (1)..(33)

<400> SEQUENCE: 3
gaaattaata cgactcacta tagggagacc acagcccatt gtgcaatatt ccccact          57

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: synthetic
      primer

<400> SEQUENCE: 4
cccgtaggag tctgggccgt atctca                                            26
```

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: synthetic primer

<400> SEQUENCE: 5
tgcctcccgt aggagtctgg gccgtatc                28

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: synthetic primer

<400> SEQUENCE: 6
gcccattgtg caatattccc cact                24

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence: synthetic primer

<400> SEQUENCE: 7
gcaagtcgaa cggaaaggcc tcttcggagg ta                32

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: synthetic primer

<400> SEQUENCE: 8
cgaacggaaa ggcctcttcg gaggtact                28

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: synthetic primer

<400> SEQUENCE: 9
gagtggcgaa cgggtgagta acacgtg                27

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: promoter

<400> SEQUENCE: 10
gaaattaata cgactcacta tagggagacc aca                33

<210> SEQ ID NO 11
<211> LENGTH: 59

```
<210> SEQ ID NO 11
<211> LENGTH: 59
<212> TYPE: DNA
<213> ORGANISM: Artificial Sequence
<220> FEATURE:
<223> OTHER INFORMATION: Description of Artificial Sequence: synthetic
      probe

<400> SEQUENCE: 11
tgagatacgg cccagactcc tacgggtgtg gtctccctat agtgagtcgt attaatttc      59

<210> SEQ ID NO 12
<211> LENGTH: 61
<212> TYPE: DNA
<213> ORGANISM: Artificial Sequence
<220> FEATURE:
<223> OTHER INFORMATION: Description of Artificial Sequence: synthetic
      probe

<400> SEQUENCE: 12
gatacggccc agactcctac gggaggcatg tggtctccct atagtgagtc gtattaattt     60
c                                                                    61

<210> SEQ ID NO 13
<211> LENGTH: 57
<212> TYPE: DNA
<213> ORGANISM: Artificial Sequence
<220> FEATURE:
<223> OTHER INFORMATION: Description of Artificial Sequence: synthetic
      probe

<400> SEQUENCE: 13
agtggggaat attgcacaat gggctgtggt ctccctatag tgagtcgtat taatttc        57

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence: synthetic
      probe

<400> SEQUENCE: 14
tacctccgaa gaggcctttc cgttcgactt gc                                   32

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: synthetic
      probe

<400> SEQUENCE: 15
agtacctccg aagaggcctt tccgttcg                                        28

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: synthetic
      probe

<400> SEQUENCE: 16
cacgtgttac tcacccgttc gccactc                                         27

<210> SEQ ID NO 17
```

```
<211> LENGTH: 19
<212> TYPE: DNA
<213> ORGANISM: Artificial Sequence
<220> FEATURE:
<223> OTHER INFORMATION: Description of Artificial Sequence: synthetic
      probe

<400> SEQUENCE: 17
ggacctcaag acgcatgtc                                              19

<210> SEQ ID NO 18
<211> LENGTH: 31
<212> TYPE: DNA
<213> ORGANISM: Artificial Sequence
<220> FEATURE:
<223> OTHER INFORMATION: Description of Artificial Sequence: synthetic
      helper

<400> SEQUENCE: 18
ttttggtgga aagcttttgc ggtgtgggat g                                31
```

METHODS AND COMPOSITIONS FOR DETECTION OF MYCOBACTERIUM AVIUM COMPLEX SPECIES

RELATED APPLICATION

This application claims the benefit under 35 U.S.C. § 119(e) of U.S. Provisional Application Ser. No. 60/171,202, filed Dec. 15, 1999, the contents of which are hereby incorporated by reference.

FIELD OF THE INVENTION

This invention relates to in vitro diagnostic detection of pathogenic bacteria, and specifically relates to compositions and assays for amplifying nucleic acid of *Mycobacterium avium* complex (MAC) organisms (e.g., *M. avium, M. intracellulare*) by using in vitro nucleic acid amplification.

BACKGROUND OF THE INVENTION

Detection of Mycobacterium species of the *Mycobacterium avium* complex (MAC) in clinical samples is important as a diagnostic tool. *M. avium* complex organisms include *M. avium, M. intracellulare* and other species that are difficult to differentiate from these, such as *M. paratuberculosis*. MAC organisms are frequently found in clinical samples and are common causative agents of opportunistic infections in immunocompromisied individuals, such as HIV-infected individuals or individuals undergoing chemotherapy or using immunosuppressive drugs (Good et al., 1982, J. Infect. Dis. 146: 829–833; Gill et al., 1985, J. Clin. Microbiol. 22: 543–546). Therefore, assays that can detect MAC species and distinguish them from other species are important for clinical diagnosis.

Clinical diagnostic assays for Mycobacterium species often rely on time-consuming methods that analyze bacterial physical characteristics (e.g., staining and microscopic detection), physiological characteristics (e.g., growth on defined media) and/or biochemical characteristics (e.g., membrane lipid composition). Such methods often require relatively high bacterial concentrations in the sample and may require a high degree of experience and expertise to properly determine the infective species. Diagnostic assays that require in vitro growth of the bacteria are costly both in terms of delayed or inappropriate early treatment of the patient and in terms of the amount of laboratory equipment and space required to culture Mycobacterium, which is often difficult to grow in vitro.

Assays that use molecular biology techniques to detect the presence Mycobacterium nucleic acid in the sample have been introduced to increase the sensitivity and relative speed of diagnosis (U.S. Pat. Nos. 5,030,557, 5,567,587, 5,595,874, 5,601,984 and 5,677,128; PCT No. WO/95/06755). These assays may directly detect the nucleic acid sequences present in the sample or may rely on in vitro nucleic acid amplification of nucleic acids present in the sample before the detection step (U.S. Pat. Nos. 5,554,516, 5,766,849, 5,906,917, 5,908,744; European Patent Nos. EP 0528306 and EP 0818465; and PCT Nos. WO 9636733 and WO 9723618). Many in vitro nucleic acid amplification reactions require amplification oligonucleotides that serve as primers for a polymerase reaction that uses the nucleic acid present in the sample as a template. Detection of the amplified nucleic acid often requires use of specific nucleic acid probes that hybridize to the amplified sequences to produce a detectable signal or complex.

The present invention provides compositions and in vitro nucleic acid amplification methods that produce relatively long amplified nucleic acid sequences to allow detection of MAC species present in a biological sample.

SUMMARY OF THE INVENTION

According to one aspect of the invention, there is provided a method of detecting *Mycobacterium avium* complex (MAC) species present in a biological sample. The method includes the steps of: providing a biological sample containing nucleic acid from at least one MAC species selected from the group consisting of *M. tuberculosis, M. avium, M. intracellulare*, and *M. paratuberculosis*, the nucleic acid comprising 16S ribosomal RNA (rRNA) or DNA encoding 16S rRNA; amplifying the 16S rRNA or DNA in an in vitro nucleic acid amplification mixture comprising at least one polymerase activity, and at least one first primer having a sequence selected from the group consisting of SEQ ID NO:1 to SEQ ID NO:6 and at least one second primer having a sequence selected from the group consisting of SEQ ID NO:7, SEQ ID NO:8 and SEQ ID NO:9, to produce an amplified nucleic acid; and detecting the amplified nucleic acid. In one embodiment, the detecting step further comprises hybridizing the amplified nucleic acid to at least one probe and detecting a signal resulting from the amplified nucleic acid that is hybridized to the probe. In another embodiment, the detecting step uses at least one labeled probe comprising sequence complementary to a portion of the amplified nucleic acid. Another embodiment of the method further includes the step of using at least one capture oligonucleotide that specifically hybridizes to nucleic acid from at least one MAC species to bind the nucleic acid from the MAC species to an immobilized nucleic acid, to purify the nucleic acid from the MAC species from other components in the sample before the amplifying step. In another embodiment, the amplifying step amplifies 16S rRNA from *M tuberculosis, M. avium, M. intracellulare, M. paratuberculosis* or any combination thereof. In some embodiments of the method, the amplifying step uses a combination selected from the group consisting of: the first primer having the sequence of SEQ ID NO:1, and the second primer having the sequence of SEQ ID NO:7; the first primer having the sequence of SEQ ID NO:1, and the second primer having the sequence of SEQ ID NO:8; the first primer having the sequence of SEQ ID NO:1, and the second primer having the sequence of SEQ ID NO:9; the first primer having the sequence of SEQ ID NO:2, and the second primer having the sequence of SEQ ID NO:7; the first primer having the sequence of SEQ ID NO:2, and the second primer having the sequence of SEQ ID NO:8; the first primer having the sequence of SEQ ID NO:2, and the second primer having the sequence of SEQ ID NO:9; the first primer having the sequence of SEQ ID NO:3, and the second primer having the sequence of SEQ ID NO:7; the first primer having the sequence of SEQ ID NO:3, and the second primer having the sequence of SEQ ID NO:8; the first primer having the sequence of SEQ ID NO:3, and the second primer having the sequence of SEQ ID NO:9; the first primer having the sequence of SEQ ID NO:4, and the second primer having the sequence of SEQ ID NO:7; the first primer having the sequence of SEQ ID NO:4, and the second primer having the sequence of SEQ ID NO:8; the first primer having the sequence of SEQ ID NO:4, and the second primer having the sequence of SEQ ID NO:9; the first primer having the sequence of SEQ ID NO:5, and the second primer having the sequence of SEQ ID NO:7; the first primer having the sequence of SEQ ID NO:5, and the second primer having the sequence of SEQ ID NO:8; the first primer having the sequence of SEQ ID NO:5, and the second primer having the sequence of SEQ ID NO:9; the first primer having the sequence of SEQ ID NO:6, and the second primer having the sequence of SEQ ID NO:7; the first primer having the sequence of SEQ ID NO:6, and the second primer having the sequence of SEQ ID NO:8; and the first primer having the sequence of SEQ ID NO:6, and the second primer having the sequence of SEQ ID NO:9. In other embodiments, the amplifying step uses a combination of at least one first primer having a sequence selected from the group consisting of SEQ ID NO:1 to SEQ ID NO:3 and at least one second primer having a sequence selected from the group consisting of SEQ ID NO:7, SEQ ID NO:8 and SEQ ID NO:9. Some preferred embodiments use a combination selected from the group consisting of: the first primer having the sequence of SEQ ID NO:1, and the second primer having the sequence of SEQ ID NO:7; the first primer having the sequence of SEQ ID NO:1, and the second primer having the sequence of SEQ ID NO:8; the first primer having the sequence of SEQ ID NO:1, and the second primer having the sequence of SEQ ID NO:9; the first primer having the sequence of SEQ ID NO:2, and the second primer having the sequence of SEQ ID NO:7; the first primer having the sequence of SEQ ID NO:2, and the second primer having the sequence of SEQ ID NO:8; the first primer having the sequence of SEQ ID NO:2, and the second primer having the sequence of SEQ ID NO:9; the first primer having the sequence of SEQ ID NO:3, and the second primer having the sequence of SEQ ID NO:7; the first primer having the sequence of SEQ ID NO:3, and the second primer having the sequence of SEQ ID NO:8; and the first primer having the sequence of SEQ ID NO:3, and the second primer having the sequence of SEQ ID NO:9. In other embodiments, the amplifying step uses transcription-mediated amplification and a combination of primers selected from the group consisting of: the first primer having the sequence of SEQ ID NO:1, and the second primer having the sequence of SEQ ID NO:7; the first primer having the sequence of SEQ ID NO:1, and the second primer having the sequence of SEQ ID NO:8; the first primer having the sequence of SEQ ID NO:1, and the second primer having the sequence of SEQ ID NO:9; the first primer having the sequence of SEQ ID NO:2, and the second primer having the sequence of SEQ ID NO:7; the first primer having the sequence of SEQ ID NO:2, and the second primer having the sequence of SEQ ID NO:8; the first primer having the sequence of SEQ ID NO:3, and the second primer having the sequence of SEQ ID NO:7; the first primer having the sequence of SEQ ID NO:3, and the second primer having the sequence of SEQ ID NO:8; and the first primer having the sequence of SEQ ID NO:3, and the second primer having the sequence of SEQ ID NO:9.

Another aspect of the invention is a composition for amplifying 16S rRNA sequence or DNA encoding 16S rRNA from at least one *Mycobacterium avium* complex (MAC) species comprising one or more oligonucleotides having a base sequence selected from the group consisting of SEQ ID NO:1 to SEQ ID NO:9. In one embodiment, the composition further comprises at least one oligonucleotide for detecting amplified MAC 16S rRNA sequence or DNA encoding 16S rRNA comprising one or more oligonucleotides having a base sequence selected from the group consisting of SEQ ID NO:11 to SEQ ID NO:18.

Another aspect of the invention is a kit containing one or more oligonucleotides having a base sequence selected from the group consisting of SEQ ID NO:1 to SEQ ID NO:9. In one embodiment, the kit further comprises one or more oligonucleotides having a base sequence selected from the group consisting of SEQ ID NO:11 to SEQ ID NO:18.

DETAILED DESCRIPTION

Diagnostic assays that rely on in vitro nucleic acid amplification must specifically amplify the intended target nucleic acid while avoiding amplification of contaminating nucleic acids that may be airborne or present in water, reagents or laboratory ware that is used in the assay. Amplification of contaminating nucleic acids could result in false positive results that would lead to misdiagnosis or unnecessary patient treatment.

False positive results may occur if the sample contains nucleic acid resulting from non-MAC Mycobacterium species or other bacteria that contain similar sequences (e.g., *M. fortuitum*) and are often environmental contaminants. Contaminating nucleic acids are generally partially degraded sequences (i.e., relatively short) compared to the target sequence present in the intact MAC organism present in the biological sample. If relatively short MAC sequences are amplified, the contaminating and/or degraded sequences present in the sample may also be amplified, leading to false positive results. Contaminating sequences that can be amplified but not detected in the assay may also compete with the MAC target for primers and/or nucleic acid polymerization substrates, leading to false negative results.

To avoid amplification of shorter contaminating nucleic acid, the present invention uses primers that hybridize specifically to a target sequence such that a relative long sequence (e.g., greater than 200 residues) located between the primer binding sites is amplified. There exists a need for compositions and methods that can amplify relatively long stretches of MAC target sequences to be detected, thus producing amplified nucleic acid for reliable detection of MAC species present in a sample.

The present invention includes amplification oligonucleotides and in vitro nucleic acid amplification methods that use these oligonucleotides as amplification primers to detect MAC species in a sample. These oligonucleotide primers specifically amplify relative long stretches (about 280 to 320 nt) of 16S ribosomal RNA (rRNA) or genomic DNA encoding ribosomal RNA sequences in in vitro amplification methods. Biological samples that may contain such target sequences are preferably derived from humans, and more preferably are processed sputum samples. The present methods may be combined with additional oligonucleotide compositions and methods that aid in the amplification or detection of the amplified MAC sequences. For example, MAC target sequences present in a sample may be partially purified from other components of the sample before amplification by using additional nucleic acid oligomers to select the MAC sequences (sometimes called "capture oligonucleotides"). Similarly, detection of the amplified nucleic acids may rely on labeled or unlabeled nucleic acid oligomers that hybridize specifically to the amplified MAC nucleic acids ("probes" or "labeled probes").

The nucleic acid sequences of the present invention are useful for amplifying relatively long nucleic acid sequences of MAC species, thus allowing detection of MAC species while avoiding the problems associated with amplifying short segments of contaminating nucleic acids described above. Thus, the compositions and methods of the present invention are useful for detecting infections caused by MAC organisms, while limiting the incidence of false positives that may result from contaminating nucleic acids in the sample. Moreover, by amplifying relatively long target sequences, even if the amplified sequence is partially degraded it may still be specifically detected (i.e., retain sufficient sequence information), thus avoiding false negative results. Similarly, the relatively long amplified sequences produced by the compositions and methods of the present invention are more useful for specific detection and identification of MAC species, distinguished from other closely-related Mycobacterium species. To aid in understanding terms used in describing this invention, the following definitions are provided.

By "biological sample" is meant any tissue or material derived from a living or dead human which may contain Mycobacterium nucleic acid or any bacterial culture derived from such material. For example, a sample may be sputum, respiratory tissue or exudates, peripheral blood, plasma or serum, cervical swab samples, biopsy tissue, gastrointestinal tissue, urine, feces, semen or other body fluids, tissues or bacterial cultures (in liquid or on solid media). To prepare the sample for analysis, the biological sample may be treated to physically disrupt cell structure and release intracellular nucleic acids into a solution that may contain other components (e.g., enzymes, buffers, salts, detergents and the like). Such methods are well known in the art (e.g., U.S. Pat. Nos. 5,374,522, 5,641,632, 5,846,701).

By "nucleic acid" is meant a multimeric compound comprising nucleosides or nucleoside analogs that have nitrogenous heterocyclic bases, or base analogs, where the nucleosides are covalently linked via a backbone structure to form a polynucleotide. Nucleic acid includes conventional ribonucleic acid (RNA) and deoxyribonucleic acid (DNA), and analogs thereof. A nucleic acid backbone may comprise a variety of known linkages, including, for example, one or more of sugar-phosphodiester linkages, peptide-nucleic acid bonds (PCT No. WO 95/32305), phosphorothioate linkages, methylphosphonate linkages or combinations thereof. Sugar moieties of the nucleic acid may be ribose or deoxyribose, or similar compounds containing substitutions, e.g., 2' methoxy substitutions and/or 2' halide substitutions. Nitrogenous bases may be conventional bases (A, G, C, T, U), known analogs thereof (e.g., inosine (I) and others, such as described in *The Biochemistry of the Nucleic Acids* 5–36, Adams et al., ed., 11$^{th}$ ed., 1992), or known derivatives of purine or pyrimidine bases (PCT No. WO 93/13121) and "abasic" residues in which the backbone includes no nitrogenous base for one or more residues (U.S. Pat. No. 5,585,481). A nucleic acid may comprise only conventional sugars, bases and linkages, as found in RNA and DNA, or may include both conventional components and substitutions (e.g., conventional bases linked via a methoxy backbone, or a nucleic acid containing a mixture of conventional bases and one or more base analogs). For all of the sequences presented herein as DNA sequences, it will be understood that the disclosed sequence also discloses the RNA equivalent (substituting a U for T residues), the reverse sequence and the reverse complement of the disclosed sequence.

By "oligonucleotide" or "oligomer" is meant a nucleic acid having generally less than 1,000 residues, including polymers in a size range having a lower limit of about 2 to 5 nucleotide residues and an upper limit of about 500 to 900 nucleotide residues. Preferred oligomers are in a size range having a lower limit of about 5 to about 15 residues and an upper limit of about 50 to 600 residues; more preferably, in a range having a lower limit of about 10 residues and an upper limit of about 100 residues. Oligomers may be purified from naturally occurring sources, but preferably are synthesized using well-known methods.

By "amplification oligonucleotide" or "amplification oligomer" is meant an oligonucleotide that hybridizes to a target nucleic acid, or its complement, and participates in an in vitro nucleic acid amplification reaction. Preferably, an amplification oligonucleotide contains at least about 10 contiguous bases, and more preferably at least about 12 contiguous bases, that are complementary to a region of the target nucleic acid sequence (or its complement). The contiguous bases preferably are complementary to at least 80%, more preferably at least 90%, of the target sequence site to which the amplification oligonucleotide binds. An amplification oligonucleotide is preferably about 10 to about 60 bases long and may include modified nucleotides or base analogs, or modified backbone linkages.

Amplification oligonucleotides and oligomers may be referred to as "primers" or "promoter primers." A "primer" refers generally to an oligonucleotide that hybridizes to a template nucleic acid and has a 3' end that is extended in a polymerization reaction, usually an enzyme-mediated reaction. The 5' region of the primer may be non-complementary to the target nucleic acid and include additional bases, such as a promoter sequence (hence referred to as a "promoter primer"). Those skilled in the art will appreciate that any oligomer that can function as a primer can be modified to include a 5' promoter sequence, and thus could function as a promoter primer. Similarly, any promoter primer can serve as a primer independent of its promoter functions.

By "amplification" is meant any known in vitro procedure for obtaining multiple copies of a target nucleic acid sequence, its complement or fragments thereof that relies on a polymerase-mediated extension of an amplification oligonucleotide or primer. In vitro nucleic acid amplification refers to production of amplified sequences that may contain less than the complete target region sequence or its complement. Such amplification methods include, for example, transcription-mediated amplification (TMA), replicase-mediated amplification, polymerase chain reaction (PCR) amplification and strand-displacement amplification (SDA). Replicase-mediated amplification uses self-replicating RNA molecules, and a replicase such as QB-replicase specific for the self-replicating RNA (U.S. Pat. No. 4,786,600; PCT No. WO 90/14439). PCR amplification uses DNA polymerase, primers and a series of thermal cycling reactions to synthesize multiple copies of the two complementary strands of DNA or cDNA (U.S. Pat. Nos. 4,683,195, 4,683,202, and 4,800,159; *Methods in Enzymology*, 1987, Vol. 155: 335–350). SDA uses a primer that contains a recognition site for a restriction endonuclease such that the endonuclease nicks one strand of a hemimodified DNA duplex that includes the target sequence, followed by amplification in a series of primer extension and strand displacement steps (Walker et al., 1992, *Proc. Natl. Acad. Sci. USA* 89:392–396; and U.S. Pat. No. 5,422,252).

By "transcription-mediated amplification" or "transcription-associated amplification" is meant any type of in vitro nucleic acid amplification that uses an RNA polymerase to produce multiple RNA transcripts from a nucleic acid template. These methods generally employ an RNA polymerase activity, a DNA polymerase activity, deoxyribonucleoside triphosphates, ribonucleoside triphosphates, and a promoter primer and a second non-promoter primer, and may optionally include one or more additional oligonucleotides (sometimes referred to as "helpers"). These methods are well known in the art, as disclosed in detail elsewhere (U.S. Pat. Nos. 5,399,491 and 5,554,516; U.S. Pat. No. 5,437,990; U.S. Pat. No. 5,130,238; U.S. Pat. Nos. 4,868,105 and 5,124,246; PCT Nos. WO 93/22461, WO 94/03472, WO 95/03430, WO 88/01302 and WO 88/10315). Although transcription-mediated amplification (TMA) is preferably used in embodiments of the present invention, those skilled in the art will understand that the oligonucleotide primer sequences of the present invention may be readily used in other in vitro amplification methods based on primer extension by a polymerase. Preferred TMA methods have been described in detail previously (U.S. Pat. Nos. 5,399,491 and 5,554,516; PCT Nos. WO 93/22461, WO 94/03472 and WO 95/03430).

By "probe" is meant a nucleic acid oligomer that hybridizes specifically to a target sequence in a nucleic acid or its complement, preferably in an amplified nucleic acid, under conditions that promote hybridization, thereby allowing detection of the nucleic acid. Detection may either be direct (i.e., resulting from a probe hybridizing directly to the target sequence or amplified nucleic acid) or indirect (i.e., resulting from a probe hybridizing to an intermediate molecular structure that links the probe to the target sequence or amplified nucleic acid). A probe's "target" generally refers to a sequence within (i.e., a subset of) the amplified nucleic acid sequence, that hybridizes specifically to at least a portion of a probe oligomer using hydrogen bonding (i.e., base pairing). "Sufficiently complementary" sequences allow stable hybridization of a probe oligomer to a target sequence in selected hybridization conditions, even if the two sequences are not 100% complementary. A probe may be labeled or unlabeled, depending on the detection method used.

By "sufficiently complementary" is meant a contiguous nucleic acid base sequence that hybridizes to another base sequence by hydrogen bonding between a series of complementary bases. Complementary sequences may be complementary at each position using standard base pairing (e.g., G:C, A:T or A:U pairing) or may contain one or more residues that are not complementary using standard hydrogen bonding (including abasic residues), but in which the complementary sequence specifically hybridizes with another base sequence in appropriate hybridization conditions. Contiguous bases are preferably at least about 80%, more preferably at least about 90% complementary to a sequence to which the oligomer hybridizes. Appropriate hybridization conditions are well known to those skilled in the art and can be readily predicted based on sequence composition and conditions, or determined empirically by using routine testing (see Sambrook et al., *Molecular Cloning, A Laboratory Manual*, $2^{nd}$ ed. (Cold Spring Harbor Laboratory Press, Cold Spring Harbor, N.Y., 1989) at §§ 1.90–1.91, 7.37–7.57, 9.47–9.51 and 11.47–11.57, particularly at §§ 9.50–9.51, 11.12–11.13, 11.45–11.47 and 11.55–11.57).

By "separating" or "purifying" is meant that one or more components of the biological sample are removed from one or more other components in the sample. Sample components include nucleic acids in a generally aqueous solution that may include other materials (e.g., proteins, carbohydrates, lipids). Preferably, a separating or purifying step for nucleic acid removes at least about 70%, more preferably at least about 90% and, even more preferably, at least about 95% of the other sample components.

Purifying a target nucleic acid may be referred to as "target capture" (see PCT No. WO 98/50583). By "capture oligonucleotide" or "capture oligomer" or "capture probe" is meant at least one nucleic acid oligomer that provides means for specifically joining a target sequence and an immobilized oligomer by using base pair hybridization. By "immobilized probe" or "immobilized nucleic acid" or "immobilized oligomer" is meant a nucleic acid that joins, directly or indirectly, a capture oligomer to a solid support to facilitate separation of bound target sequence from unbound material in a sample.

By "label" is meant a molecular moiety or compound that can be detected or lead to a detectable response. A label is joined, directly or indirectly, to a nucleic acid probe or to the nucleic acid to be detected (e.g., to the amplified nucleic acid). Direct labeling can occur through bonds or interactions that link the label to the probe (e.g., covalent bonds or non-covalent interactions). Indirect labeling can occur through use of a bridging moiety or "linker" (e.g., additional oligonucleotide) which is directly or indirectly labeled. Labels include any known detectable moiety (e.g., radionuclide, ligand, such as biotin or avidin, enzyme or enzyme substrate, reactive group, chromophore, such as a dye or colored particle, luminescent compound such as a bioluminescent, phosphorescent or chemiluminescent compound, or fluorescent compound). Preferably, the label on a labeled probe is detectable in a homogeneous assay system (i.e., in a mixture, bound labeled probe exhibits a detectable signal compared to unbound labeled probe; see U.S. Pat. Nos. 5,283,174 and 5,639,604). Preferred labels for use in a homogenous assay are chemiluminescent compounds, more preferably acridinium ester ("AE") compounds (U.S. Pat. Nos. 5,656,207, 5,658,737 and 5,639,604). Methods of attaching labels to nucleic acids and detecting labels are well known in the art (e.g., see Sambrook et al., *Molecular Cloning, A Laboratory Manual*, $2^{nd}$ ed. (Cold Spring Harbor Laboratory Press, Cold Spring Harbor, N.Y., 1989), Chapter 10; U.S. Pat. Nos. 5,658,737, 5,656,207, 5,547,842, 5,283,174 and 4,581,333; and EP Pat. App. No. 0 747 706).

A "homogeneous detectable label" refers to a label whose presence can be detected based on whether the label is on a probe hybridized to a target sequence. That is, a homogeneous detectable label can be detected without physically removing hybridized from unhybridized forms of the labeled probe. Known homogeneous detectable labels and methods of detecting them are described in detail in U.S. Pat. Nos. 5,283,174, 5,656,207 and 5,658,737.

By "consisting essentially of" is meant that additional component(s), composition(s) or method step(s) that do not materially change the basic and novel characteristics of the present invention may be included in the compositions or methods of the present invention. Such characteristics include the ability to produce relatively long amplified Mycobacterium sequences that allow specific detection of MAC species sequences. Components, compositions, or method steps that have a material effect on the basic characteristics of the present invention would fall outside of this term.

Unless defined otherwise, all scientific and technical terms used herein have the same meaning as commonly understood by those skilled in the relevant art. General definitions of many such terms are found in, for example *Dictionary of Microbiology and Molecular Biology*, $2^{nd}$ ed. (Singleton et al., 1994, John Wiley & Sons, New York, N.Y.) or *The Harper Collins Dictionary of Biology* (Hale & Marham, 1991, Harper Perennial, New York, N.Y.). Unless otherwise described, the techniques employed or contemplated herein are standard methodologies well known to those of ordinary skill in the art.

The present invention includes compositions, specifically nucleic acid amplification oligomers, individually or in combinations, that are used in in vitro nucleic acid amplification methods used to detect MAC species. The present invention also includes methods using such amplification oligomers in in vitro nucleic acid amplification to detect MAC species. Optionally, additional DNA sequences may be used to capture MAC target sequences from a biological sample before amplification of the MAC sequence. A variety of methods are known in the art for specifically detecting amplified nucleic acid. In embodiments of the present invention, a labeled probe is preferably used to detect the amplified MAC nucleic acid sequences. More preferably, the labeled probe detects the amplified MAC nucleic acid in a homogeneous detection assay.

Primer sequences of the present invention are used to amplify relatively long sequences contained within 16S rRNA sequences of Mycobacterium. Generally, primers were designed by comparing known 16S rRNA sequences from *M. tuberculosis*, *M. avium* and *M. intracellulare* and selecting regions in which the sequences were relatively conserved and sufficiently spaced apart to allow amplification of at least 200 residues of rRNA sequence. That is, the sequences were aligned by matching regions of the same or similar sequences and the sequences were compared using well known molecular biology techniques. Although sequence comparisons may be facilitated by using computerized algorithms, those skilled in the art can readily perform such comparisons manually. When the relatively conserved regions of the compared sequences were selected, specific oligomers were designed containing a subset of the conserved sequence having a GC content of about 40% to 60%, a $T_m$ greater than 60° C. and relatively little or no predicted secondary structure (e.g., hairpin structures), all determined by using standard methods. Designed oligomers having sequences of SEQ ID NO:1 to SEQ ID NO:3 and SEQ ID NO:7 to SEQ ID NO:9 were synthesized.

Amplifying the MAC target region using at least two primers can be accomplished using a variety of known nucleic acid amplification reactions, but preferred embodiments use an isothermal transcription-mediated amplification (TMA) reaction (U.S. Pat. Nos. 5,399,491 and 5,554,516). Using this method, many strands of nucleic acid are produced from a single copy of target nucleic acid, thus permitting detection of the amplified target by using known detection methods. Briefly, TMA uses a promoter-primer that contains a 5' promoter sequence, a second primer, a reverse transcriptase, an RNA polymerase, substrates for nucleic acid polymerization (dNTPs and rNTPs) and appropriate salts and buffers in solution to produce multiple RNA transcripts from a nucleic acid template. The promoter-primer hybridizes specifically to the target RNA and reverse transcriptase creates a first strand cDNA by extension from the 3' end of the promoter-primer. The cDNA hybridizes with the second primer. Hybridization may be facilitated by denaturing the RNA-DNA duplex or by using RNase H activity associated with the reverse transcriptase to remove the RNA in the RNA-DNA duplex. The second primer binds to the cDNA distal to the first primer and a new strand of DNA is synthesized from the 3' end of the second primer using reverse transcriptase, producing a double-stranded DNA with a functional promoter sequence at one end. RNA polymerase binds to the double-stranded promoter sequence and transcription produces multiple transcripts, i.e., amplified products of the target sequence or "amplicons." Amplicons then are further used in the TMA process, serving as a template for a new cycle of replication, thus generating large amounts of single-stranded amplified nucleic acid (i.e., about 100 to 3,000 copies of RNA transcripts synthesized from a single template).

Primer sequences (SEQ ID NO:1 to SEQ ID NO:9) bind specifically to a MAC target sequence or a complement of a MAC target sequence, although primer sequences may contain sequences that do not bind to the target sequence or its complement. In particular, T7 promoter primers (SEQ ID NO:1 to SEQ ID NO:3) include a 5' T7 promoter sequence (shown separately in SEQ ID NO:10) attached to a 3' sequence that binds to the target or its complement. Those skilled in the art will appreciate that a target-specific primer sequence, with or without an attached promoter sequence, may be useful as a primer in a variety of in vitro amplification conditions.

Briefly, the assays of the present invention include the steps of providing a biological sample containing MAC target rRNA or DNA encoding 16S rRNA, optionally using target capture to partially purify the target, in vitro nucleic acid amplification and detection of the amplified nucleic acid products. In preferred embodiments that use TMA, illustrated in examples that follow, the amplification mixture includes MAC target rRNA, at least one promoter primer that hybridizes to the target sequence, at least one second primer that hybridizes specifically to a first strand cDNA made from the target using the T7 promoter primer, and substrates and cofactors for enzymatic polymerization by using reverse transcriptase and T7 RNA polymerase.

The amplified nucleic acid products may be detected using any of a variety of known methods, including, for example, gel analysis or hybridizing the amplified products, or portions thereof, to at least one complementary probe sequence. The probe may be an oligonucleotide that contains a reverse complementary sequence of a primer sequence (SEQ ID NO:11 to SEQ ID NO:16). Those skilled in the art can readily determine other probe sequences that hybridize to amplified MAC sequences produced using the primers disclosed herein (i.e., any sequence that hybridizes specifically to a portion of the amplified target produced by using any two functionally compatible amplification oligonucleotides of the present invention). For detection of the amplified nucleic acid, the probe may be labeled or the amplification product may be labeled. For example, a labeled probe may be hybridized to the amplified nucleic acid and detected in a homogeneous system (U.S. Pat. Nos. 5,185,439, 5,283,174, 5,585,481 and 5,639,604). In another example, an immobilized probe may be used to capture and labeled amplified nucleic acids that are then detected in the resulting labeled nucleic acid:immobilized probe complex.

Target capture is optionally included in the method to increase the concentration or purity of the MAC target nucleic acid before in vitro amplification. Preferably, target capture involves a relatively simple method of hybridizing and isolating the target nucleic acid, as described in detail in PCT No. WO 98/50583. Briefly, an oligonucleotide attached to a solid support is mixed with the target nucleic acid under appropriate hybridization conditions to allow the target nucleic acid to be releasably attached to the solid support. Target capture may result from direct hybridization between the MAC nucleic acid and the immobilized oligonucleotide on the solid support, or may be indirectly via one or more oligonucleotides forming a hybridization complex that links the MAC nucleic acid to the immobilized oligonucleotide. A preferred solid support is a particle that can be readily separated from the solution (e.g., a paramagnetic particle that can be isolated from the mixture by applying a magnetic field to the vessel). The MAC target nucleic acid linked to the solid support is washed and then amplified upon exposure to the appropriate primers, substrates and enzymes in an in vitro amplification reaction.

A typical amplification assay that is an embodiment of the present invention includes the following steps and conditions. A sample contains either a known amount of purified rRNA isolated from *M. avium* in a buffer solution or contains bacteria (e.g., 0.5 ml of sputum sediment or bacterial culture). For samples containing purified rRNA target, the assay proceeds directly to in vitro nucleic acid amplification because no cell lysis is needed. For bacteria-containing samples, the sample is mixed with a lysis buffer (e.g., 10 mM HEPES, 0.25–0.5% (w/v) lithium lauryl sulfate, pH 8) in a tube and intracellular nucleic acid is released using standard methods (e.g., sonication). For example, a 50 µl sample of sputum sediment was mixed with 200 µl of the lysis buffer and the sample was incubated at room temperature for 15 min in a sonication water bath, optionally followed by heat killing of remaining organisms by incubating at 95° C. for 15 min. Such sample preparation methods are well known (U.S. Pat. Nos. 5,364,763, 5,374,522 and 5,837,452).

When target capture is optionally included to partially purify MAC target nucleic acid from other sample components in the mixture, the procedure is substantially as described in PCT No. WO 98/50583. Briefly, 250 µl of the bacterial lysate is mixed with an equal volume of buffer containing a target capture oligomer (usually 5 pmols) that is complementary to part of the 16S rRNA sequence to be amplified, and 50 µg of paramagnetic particles (0.7–1.05µ particles, Seradyn, Indianapolis, Ind.) to which are attached immobilized probe that is complementary to at least part of the target capture oligomer (e.g., poly-dT$_{14-24}$). The target capture mixture is heated (e.g., 60–70° C. for 15–20 min) and then cooled to room temperature to allow hybridization, after which a magnetic field is applied (5 min) to attract magnetic particles with the attached complex containing the MAC target RNA to a location on the reaction container (U.S. Pat. No. 4,895,650). The particles are washed twice with a washing buffer (e.g., 1 ml of 10 mM HEPES, 6.5 mM NaOH, 1 mM EDTA, 150 mM NaCl, 0.1% (w/v) sodium lauryl sulfate) and again separated. Particles with attached target can be used directly in a nucleic acid amplification reaction.

In vitro nucleic acid amplification using TMA was performed using the followiing conditions (see also U.S. Pat. Nos. 5,399,491 and 5,554,516). Generally, the sample containing target (either purified 16S rRNA, cell lystate or washed particles) was mixed with amplification reagent solution (40 mM Tris-HCl, pH 7.5, 17.5 mM KCl, 20 mM MgCl$_2$, 5% polyvinylpyrrolidone, 1 mM each dNTP, 4 mM each rNTP) and at least two primer oligomers (at least one promoter primer and a second primer, at 2.5 to 30 pmols of each), and covered with a layer (200 µl) of inert oil to prevent evaporation. In some assays, the amplification reagent solution substituted 74 mM Tris-HCl for 40 mM Tris-HCl, 6.15 mM MgCl$_2$ for 20 mM MgCl$_2$, 23 mM K-acetate for 20 mM KCl, 0.62 mM dNTP for 1 mM dNTP and added 7.7% (v/v) DMSO. The mixture was incubated at 90–100° C. for 15 min, then at 42° C. for 5 min. Then, 25 µl of enzyme reagent was added (a solution of 250 U of MMLV reverse transcriptase and 500 U of T7 RNA polymerase per reaction, in 50 mM HEPES, 1 mM EDTA, 10% (v/v) Triton™ X-100 or Tween™-40, 120 mM KCl, and 20% (v/v) glycerol). The amplification mixture was shaken gently and incubated at 42° C. for 1–2 hr. Negative controls consisted of all of the same reagents but used an equal volume of water or buffer without MAC nucleic acid in place of the MAC target.

Amplified sequences were detected generally using an acridinium ester (AE)-labeled probe (usually 5.5 pmol per reaction) which was detected by chemiluminescence in a suitable luminometer (e.g., LEADER™ luminometer, Gen-Probe Incorporated, San Diego, Calif.) and expressed in relative light units (RLU) substantially as described previously (U.S. Pat. No. 5,658,737 at column 25, lines 27–46; Nelson et al., 1996, Biochem. 35:8429–8438 at 8432). Generally, the average (mean) of detected RLU for replicate assays are reported. The probes were SEQ ID NO:17 and helper probe SEQ ID NO:18.

The following non-limiting examples demonstrate aspects of preferred embodiments of the present invention.

EXAMPLE 1

In Vitro Amplification of *M. avium* rRNA Using Different Primers

Using the amplification and labeled probe detection methods described above, the efficiencies of transcription-mediated amplification were tested using different combinations and concentrations of promoter primers and second primers.

In a first set of reactions, the promoter primer and second primer were present in the reaction at 7.5, 15 or 30 pmols each per reaction; and the negative control for each set of conditions contained no target RNA. The primers used were a T7 promoter primer of SEQ ID NO:1 (GAAATTAATACGACTCACTATAGGGAGACCACA CCCGTAGGAGTCTGGGCCGTATCTCA) and a second primer of SEQ ID NO:7 (GCAAGTCGAACGG-AAAGGCCTCTTCGGAGGTA). The target sequences were purified *M. avium* 16S rRNA present in the amplification reaction at 400 or 2000 copies per reaction (1 fg or 5 fg, respectively). For each set of conditions, three replicate assays were performed. Amplification (for 2 hr at 42° C.) was assessed based on the relative light units (RLU) detected after hybridization of the amplification products with an AE-labeled probe (SEQ ID NO: 17) with an unlabeled helper probe (SEQ ID NO:18), using previously described detection methods (U.S. Pat. Nos. 5,595,874 and 5,639,604). Table 1 presents the results obtained with these combinations of amplification oligonucleotides. Each result represents the mean of three replicate assays for each condition.

TABLE 1

Detected RLU (mean) following amplification of *M. avium* rRNA Using SEQ ID NO:1 and SEQ ID NO:7

| Primer Concentration | 0 Copies of Target RNA | 400 Copies Target RNA | 2000 Copies Target RNA |
|---|---|---|---|
| 7.5 pmol | 1,504 | 426,443 | 1,279,701 |
| 15 pmol | 1,628 | 148,199 | 747,288 |
| 30 pmol | 1,960 | 76,777 | 472,662 |

These results show that all of the concentrations of primer and promoter primer in the amplification reactions produced significantly more detectable amplification products than in the negative control reactions that contained no target RNA. Under these conditions, a concentration of 7.5 pmol each of the promoter primer and second primer gave the highest amount of detectable amplification products for both concentrations of target tested.

A second set of reactions were performed substantially the same as the first set, using the same primer and target concentrations, but using a different combination of primer sequences. The promoter primer was SEQ ID NO:3 (GAAATTAATACGACTCACTATAGGGAGACCACA GCCCATTGTGCAATATTCCCCACT) and the second primer was SEQ ID NO:9 (GAGTGGCGMCGGG-TGAGTMCACGTG). The results in Table 2 show the mean RLU detected for each of the conditions for three replicate assays per each condition.

TABLE 2

Detected RLU (mean) following amplification of *M. avium* rRNA Using SEQ ID NO:3 and SEQ ID NO:9

| Primer Concentration | 0 Copies of Target RNA | 400 Copies Target RNA | 2000 Copies Target RNA |
|---|---|---|---|
| 7.5 pmol | 1,535 | 72,765 | 403,905 |
| 15 pmol | 1,314 | 25,080 | 176,081 |
| 30 pmol | 1,461 | 12,072 | 50,278 |

These results show that another set of primers can also effectively amplify the 16S MAC target compared to the negative control, although the amplification results with this combination of primers produced less amplified product that those used in the first set of experiments. As for the earlier combination of primers, the combination of SEQ ID NO:3 and SEQ ID NO:9 gave optimal amplification using the lowest concentration of primers tested (7.5 pmols each).

EXAMPLE 2

In Vitro Amplification of MAC rRNA Using Different Combinations of Primers

Using the amplification and labeled probe detection methods substantially as described in Example 1, the efficiencies of transcription-mediated amplification were tested using different combinations of primers: SEQ ID NO:1 with SEQ ID NO:8, and SEQ ID NO:1 with SEQ ID NO:9.

For the first combination, the T7 promoter primer was SEQ ID NO:1 and second primer was SEQ ID NO:8 (CGAACGGAAAGGCCTCTTCGGAGGTACT), each present in each reaction at 7.5, 15 or 30 pmols; the negative control reactions for each primer concentration contained no target RNA. The target sequences were purified *M. avium* 16S rRNA at 400 or 2000 copies per reaction. For each set of conditions, three replicate assays were performed. For the second combination, the T7 promoter primer was SEQ ID NO:1 and second primer was SEQ ID NO:9 (GAGTGGCGMCGGGTGAGTMCACGTG), with each reaction performed as for the first combination reactions. For each condition, triplicate assays were performed. Table 3 presents the results (mean RLU) obtained with these combinations of amplification oligonucleotides.

TABLE 3

Amplified MAC Nucleic Acid Detected (mean RLU)

| Primers | Primer Concentration | MAC Target rRNA (copies per reaction) | | |
|---|---|---|---|---|
| | | 0 | 400 | 2,000 |
| SEQ ID NO:1 SEQ ID NO:8 | 7.5 pmol | 2,040 | 456,230 | 1,189,819 |
| SEQ ID NO:1 SEQ ID NO:8 | 15 pmol | 1,745 | 500,643 | 1,190,691 |
| SEQ ID NO:1 SEQ ID NO:8 | 30 pmol | 2,967 | 187,108 | 745,976 |
| SEQ ID NO:1 SEQ ID NO:9 | 7.5 pmol | 2,264 | 19,442 | 62,938 |
| SEQ ID NO:1 SEQ ID NO:9 | 15 pmol | 2,086 | 16,694 | 74,514 |
| SEQ ID NO:1 SEQ ID NO:9 | 30 pmol | 2,023 | 18,989 | 79,188 |

These results show that other second primers can be combined with the primer having SEQ ID NO:1 to amplify MAC target nucleic acid in vitro. The combination of SEQ ID NO:1 and SEQ ID NO:8 was more efficient for amplification of the same target nucleic acid than the combination of SEQ ID NO:1 and SEQ ID NO:9. For the former combination, primer concentrations of 7.5 and 15 pmols appeared to be optimal of those tested here.

EXAMPLE 3

In Vitro Amplification of MAC rRNA Using Different Combinations of Primers

Using the amplification and labeled probe detection methods substantially as described in Example 1, the efficiencies of transcription-mediated amplification were tested using the combinations of primers of SEQ ID NO:1 with SEQ ID NO:9, and SEQ ID NO:2 with SEQ ID NO:8.

For the first combination, the T7 promoter primer was SEQ ID NO:1 and second primer was SEQ ID NO:9, assayed as in Example 2. For the second combination, the T7 promoter primer was SEQ ID NO:2 (GAAATTAATACGACTCACTATAGGGAGACCACATG-CCTCCCGTAGGAGTCTGGGCCGTATC) and second primer was SEQ ID NO:8, each present in each reaction at 7.5,15 or 30 pmols; the negative control reactions for each primer concentration contained no target RNA. The target sequences were purified *M. avium* 16S rRNA at 400 or 2000 copies per reaction. For each set of conditions, three replicate assays were performed. Table 4 presents the results (mean RLU) obtained with these combinations of amplification oligonucleotides. Note that the negative control for the set of assays using 15 pmol of SEQ ID NO:2 and SEQ ID NO:8 primers reports the results of two replicate assays.

TABLE 4

Amplified MAC Nucleic Acid Detected (mean RLU)

| Primers | Primer Concentration | MAC Target rRNA (copies per reaction) | | |
|---|---|---|---|---|
| | | 0 | 400 | 2,000 |
| SEQ ID NO:1 SEQ ID NO:9 | 7.5 pmol | 4,994 | 29,994 | 351,732 |
| SEQ ID NO:1 SEQ ID NO:9 | 15 pmol | 4,354 | 39,681 | 78,266 |
| SEQ ID NO:1 SEQ ID NO:9 | 30 pmol | 4,321 | 62,385 | 283,414 |
| SEQ ID NO:2 SEQ ID NO:8 | 7.5 pmol | 3,505 | 261,020 | 1,716,613 |
| SEQ ID NO:2 SEQ ID NO:8 | 15 pmol | 4,227 | 336,679 | 354,382 |
| SEQ ID NO:2 SEQ ID NO:8 | 30 pmol | 4,364 | 108,722 | 870,807 |

These results show that another combination of primers (SEQ ID NO:2 and SEQ ID NO:8) also amplify MAC target nucleic acid in vitro. In these assays, the combination of SEQ ID NO:1 and SEQ ID NO:9 was more efficient for amplification than for the experiments presented in Table 3.

EXAMPLE 4

In Vitro Amplification of MAC rRNA Using SEQ ID NO:2 or SEQ ID NO:3 with SEQ ID NO:7 or SEQ ID NO:8 Primers Using the amplification and labeled probe detection methods substantially as described in Example 1, the efficiencies of transcription-mediated amplification were tested using the combinations of primers of SEQ ID NO:2 with SEQ ID NO:7, SEQ ID NO:3 with SEQ ID NO:7 and SEQ ID NO:3 with SEQ ID NO:8.

In a first set of reactions, the T7 promoter primer was SEQ ID NO:2 (see Example 3) and second primer was SEQ ID NO:7 (see Example 1). Table 5 presents the results (mean RLU) obtained with this combination of amplification oligonucleotides.

TABLE 5

Detected RLU (mean) Following MAC Nucleic Acid Amplification Using SEQ ID NO:2 and SEQ ID NO:7

| Primer Concentration | 0 Copies of Target RNA | 400 Copies Target RNA | 2000 Copies Target RNA |
| --- | --- | --- | --- |
| 7.5 pmol | 3,415 | 113,620 | 626,584 |
| 15 pmol | 4,192 | 117,838 | 496,104 |
| 30 pmol | 4,071 | 74,159 | 302,984 |

These results show that another combination of primers (SEQ ID NO:2 and SEQ ID NO:7) also amplify MAC target nucleic acid in vitro. As in the experiments reported in Example 2, the concentrations of 7.5 and 15 pmol of primers were most effective in these amplification conditions.

In a second set of experiments, using another preparation of detection reagents, the amplification of *M. avium* 16S rRNA was tested using the combinations of SEQ ID NO:3 with SEQ ID NO:7 and SEQ ID NO:3 with SEQ ID NO:8. The results of triplicate assays for each primer combination and concentration are shown in Table 6.

TABLE 6

MAC Nucleic Acid Amplification Using SEQ ID NO:3 with SEQ ID NO:7 or SEQ ID NO:8

| Primers | Primer Concentration | MAC Target rRNA (copies per reaction) | | |
| --- | --- | --- | --- | --- |
| | | 0 | 400 | 2,000 |
| SEQ ID NO:3 SEQ ID NO:7 | 7.5 pmol | 6,023 | 1,881,960 | 2,443,145 |
| SEQ ID NO:3 SEQ ID NO:7 | 15 pmol | 5,037 | 657,454 | 2,420,688 |
| SEQ ID NO:3 SEQ ID NO:7 | 30 pmol | 5,523 | 275,078 | 1,098,247 |
| SEQ ID NO:3 SEQ ID NO:8 | 7.5 pmol | 8,959 | 2,428,940 | 3,340,647 |
| SEQ ID NO:3 SEQ ID NO:8 | 15 pmol | 8,598 | 1,779,767 | 3,385,338 |
| SEQ ID NO:3 SEQ ID NO:8 | 30 pmol | 7,004 | 575,696 | 2,107,862 |

These results show that another combination of the primers is effective in MAC amplification. Although the negative control (0 copies of target) and experimental (400 and 2000 copies of target) assays all gave higher RLU than in the previous experiments, the amplified nucleic acid detected was significantly greater than the negative control. As seen with other combinations tested using these conditions, 7.5 pmol of primers was generally more efficient for amplification than higher concentrations tested.

In similar experiments, the combination of SEQ ID NO:3 and SEQ ID NO:7 were used at higher concentrations of each primer per reaction (15, 30 or 45 pmols), to amplify 0, 100, 400 or 1000 copies of MAC rRNA per reaction. Using these conditions, the higher primer concentrations (30 pmols and 45 pmols per reaction) were less efficient than 15 pmol of each primer for all concentrations of target nucleic acid tested.

EXAMPLE 5

In Vitro Amplification of MAC rRNA Using Lowered Primer and Target Concentrations Using the amplification and labeled probe detection methods substantially as described in Example 1, the efficiencies of transcription-mediated amplification were tested using the combinations of primers of SEQ ID NO:1 with SEQ ID NO:7, and SEQ ID NO:1 with SEQ ID NO:8. In these assays, primers were used at concentrations of 2.5, 5.0, 7.5 or 15 pmols of each primer in the combination. For both combinations, the T7 promoter primer was SEQ ID NO:1 (see Example 1) and the second primer was either SEQ ID NO:7 (see Example 1) or SEQ ID NO:8 (see Example 2). The target sequences were purified *M. avium* 16S rRNA at 0, 400 or 1000 copies per reaction. For each set of conditions, three replicate assays were performed. Table 7 presents the results (mean RLU) obtained with these combinations of amplification oligonucleotides.

TABLE 7

Amplified MAC Nucleic Acid Detected (mean RLU) After Amplification Using Lowered Primer and Target Concentrations

| Primers | Primer Concentration | MAC Target rRNA (copies per reaction) | | |
| --- | --- | --- | --- | --- |
| | | 0 | 400 | 1,000 |
| SEQ ID NO:1 SEQ ID NO:7 | 2.5 pmol | 3,029 | 212,560 | 1,068,251 |
| SEQ ID NO:1 SEQ ID NO:7 | 5.0 pmol | 2,900 | 88,446 | 578,234 |
| SEQ ID NO:1 SEQ ID NO:7 | 7.5 pmol | 2,502 | 13,566 | 241,774 |
| SEQ ID NO:1 SEQ ID NO:7 | 15 pmol | 2,586 | 8,999 | 216,854 |
| SEQ ID NO:1 SEQ ID NO:8 | 2.5 pmol | 3,230 | 239,390 | 916,512 |
| SEQ ID NO:1 SEQ ID NO:8 | 5.0 pmol | 3,172 | 254,414 | 360,817 |
| SEQ ID NO:1 SEQ ID NO:8 | 7.5 pmol | 3,075 | 190,152 | 667,024 |
| SEQ ID NO:1 SEQ ID NO:8 | 15 pmol | 3,576 | 109,758 | 661,296 |

These results show that combinations of primers are effective for MAC target nucleic acid amplification in vitro using less primer than in the previous examples. In these assays, the SEQ ID NO:1 and SEQ ID NO:7 combination was most effective when used at 2.5 pmols per reaction; the SEQ ID NO:1 and SEQ ID NO:8 combination was most effective when used at 2.5 or 5.0 pmols per reaction, at least for relatively few target copies per reaction (400). For both combinations, amplification was less efficient when higher concentrations of primers were used per reaction.

Similar experiments were performed using the combination of SEQ ID NO:1 and SEQ ID NO:8 at higher concentrations of each primer per reaction (30 or 45 pmols), to amplify 0, 100, 400 or 1000 copies of MAC rRNA per reaction. Using these conditions, primers at 30 pmols per reaction were more efficient for amplification of MAC nucleic acid than 45 pmols of primers per reaction. Both 30 and 45 pmols of primers were effective for amplifying as few as 100 copies of the target nucleic acid per reaction.

EXAMPLE 6

In Vitro Amplification of MAC rRNA Using Lowered Primer and Target Concentrations Using the amplification and labeled probe detection methods substantially as described in Example 5, the efficiencies of transcription-mediated amplification were tested using the combinations of primers of SEQ ID NO:3 with SEQ ID NO:7, SEQ ID NO:3 with SEQ ID NO:8, and SEQ ID NO:2 with SEQ ID NO:8. The primers were used at concentrations of 2.5, 5.0, 7.5 or 15 pmols of each primer in the combination. In these combinations, the T7 promoter primer was SEQ ID NO:1 (see Example 1) or SEQ ID NO:2 (see Example 3), and the second primer was either SEQ ID NO:7 (see Example 1) or SEQ ID NO:8 (see Example 2). The target sequences were purified *M. avium* 16S rRNA at 0, 100, 400 or 1000 copies per reaction. For each set of conditions, three replicate assays were performed. Table 8 presents the results (mean RLU of triplicate assays, except as indicated for "two assays") obtained with these combinations of amplification oligonucleotides.

TABLE 8

Amplified MAC Nucleic Acid Detected (mean RLU) After Amplification Using Lowered Primer and Target Concentrations

| Primers | Primer Concentration | MAC Target rRNA (copies per reaction) | | | |
|---|---|---|---|---|---|
| | | 0 | 100 | 400 | 1,000 |
| SEQ ID NO:3 SEQ ID NO:7 | 2.5 pmol | 7,791 | 446,924 | 1,231,247 | 2,670,330 |
| SEQ ID NO:3 SEQ ID NO:7 | 5.0 pmol | 8,772 | 316,388 | 798,598 | 2,559,093 |
| SEQ ID NO:3 SEQ ID NO:7 | 7.5 pmol | 8,024 | 213,849 | 1,163,975 | 2,088,209 |
| SEQ ID NO:3 SEQ ID NO:7 | 15 pmol | 7,736 | 165,354 | 413,745 | 1,236,161 |
| SEQ ID NO:3 SEQ ID NO:8 | 2.5 pmol | 8,100 | 552,870 | 1,278,760 | 3,156,067 |
| SEQ ID NO:3 SEQ ID NO:8 | 5.0 pmol | 7,536 | 681,501 | 1,536,807 | 3,140,628 |
| SEQ ID NO:3 SEQ ID NO:8 | 7.5 pmol | 6,986 (two assays) | 248,578 | 2,061,581 | 3,335,045 |
| SEQ ID NO:3 SEQ ID NO:8 | 15 pmol | 7,072 | 247,913 | 576,368 | 2,618,135 |
| SEQ ID NO:2 SEQ ID NO:8 | 2.5 pmol | 5,696 | 192,462 | 666,008 | 1,414,693 |
| SEQ ID NO:2 SEQ ID NO:8 | 5.0 pmol | 6,650 | 210,100 | 1,124,522 | 1,702,789 |
| SEQ ID NO:2 SEQ ID NO:8 | 7.5 pmol | 5,670 | 318,640 | 1,559,311 | 2,585,336 |
| SEQ ID NO:2 SEQ ID NO:8 | 15 pmol | 5,756 | 312,377 | 2,010,870 | 3,013,663 |

These results show that these combinations of primers are effective for MAC target nucleic acid amplification in vitro using as little as 2.5 pmol of each primer per reaction. These results also show that these primers can amplify as few as 100 copies of MAC target nucleic acid per reaction to produce detectable amplified nucleic acid.

EXAMPLE 7

Frequency of False Positives in In Vitro Amplification of MAC rRNA

This example shows that false positives do not occur at high frequency in amplification reactions as described in Examples 1 to 6. Environmental contamination may result from the presence of MAC organisms or nucleic acids in water, reagents, laboratory wares (e.g., tubes, pipetting devices) used in the assay or may enter the assay from a variety of sources (e.g., water baths, sinks, aerosols) in the laboratory. The false positive frequency due to amplification of environmental contaminants was initially estimated based on the number of reactions that provided positive signal (generally, greater than 100,000 RLU) when the reaction mixture contained no added MAC target RNA (i.e., the negative control reactions) described in Examples 1 to 6. The determined false positive frequency was 1.4% (2 of 144 reactions).

This was further extended by using the primer combination of SEQ ID NO:1 with SEQ ID NO:8, described in Examples 1 and 5, in the amplification and labeled probe detection methods substantially as described for the negative controls (i.e., without target nucleic acid) in four sets of 40 amplification assays each (160 total). In the absence of 16S rRNA from a MAC species (*M. avium*) only three assays of the 160 showed amplification results that were considered to be false positives. Thus, these primers had a false positive rate of about 1.8% in the absence of MAC target nucleic acid in these tests.

The false positive rate for the total target-negative reactions (i.e., in Examples 1 to 7) was 1.6% (5 of 304). These results show that the compositions and methods of the present invention do not have a high frequency of false positive results due to spurious environmental contamination.

EXAMPLE 8

In Vitro Amplification of MAC rRNA Using Polymerase Chain Reaction

This example shows that combinations of the MAC primers of the present invention can be used to amplify MAC specific sequence using PCR amplification. For target preparation, *M. intracellulare* and *M. avium* are grown in vitro using standard microbiology methods and about $10^6$ bacteria/ml are lysed by suspending the bacteria in 10 mM HEPES, 0.5% (w/v) lithium lauryl sulfate, pH 8 and then incubating the tube at room temperature for 15 min in a sonication water bath. The negative control for amplification is an equal volume of sterile water used in place of the target solution.

PCR amplification is performed for each target with each combination of primers in 45 µl reactions, each containing 50 mM KCl, 10 mM Tris (pH 8.3), 1.5 mM $MgCl_2$, 0.001% (w/v) gelatin, 5% (v/v) dimethylsulfoxide, 0.33 µM of each primer in a primer combination, 200 µM of each dNTP, and 0.75 U of Taq polymerase (AmpliTaq™; Perkin-Elmer, Norwalk, Conn.) Thermal cycling is performed using a first cycle at 94° C. for 5 min, then 30 cycles of 94° C. for 1 min, 55° C. for 1 min and 72° C. for 1 min, and a final cycle of 72° C. for 10 min (in a Perkin-Elmer 9600™ thermal cycler).

The combinations of primers tested include: SEQ ID NO:1 with SEQ ID NO:7; SEQ ID NO:1 with SEQ ID NO:8; SEQ ID NO:1 with SEQ ID NO:9; SEQ ID NO:2 with SEQ ID NO:7; SEQ ID NO:2 with SEQ ID NO:8; SEQ ID NO:2 with SEQ ID NO:9; SEQ ID NO:3 with SEQ ID NO:7; SEQ ID NO:3 with SEQ ID NO:8; SEQ ID NO:3 with SEQ ID NO:9; SEQ ID NO:4 with SEQ ID NO:7; SEQ ID NO:4 with SEQ ID NO:8; SEQ ID NO:4 with SEQ ID NO:9; SEQ ID NO:5 with SEQ ID NO:7; SEQ ID NO:5 with SEQ ID NO:8; SEQ ID NO:5 with SEQ ID NO:9; SEQ ID NO:6 with SEQ ID NO:7; SEQ ID NO:6 with SEQ ID NO:8; and SEQ ID NO:6 with SEQ ID NO:9.

Following PCR amplification, the amplification products are analyzed by agarose gel electrophoresis, to detect the presence or absence of a band of DNA of about 250–300 nt, relative to know size markers. No band is visible on the gel for the negative control, but for each combination of primers the appropriately sized band is seen. That is, for the combinations of SEQ ID NO:1 and SEQ ID NO:7 or SEQ ID NO:8, the band of amplified DNA is about 280 nt long; for the combination of SEQ ID NO:2 and SEQ ID NO:7 or SEQ ID NO:8, the band of amplified DNA is about 285–290 nt long; and for the combination of SEQ ID NO:3 and SEQ ID NO:7 or SEQ ID NO:8, the band of amplified DNA is about 315 nt long. All of the other combinations tested produce amplified DNA of about 280–320 nt long as detected on a gel relative to known size markers.

Following PCR amplification, the amplification products are also analyzed by hybridization with a probe that is the reverse complement of at least one of the primers used in the combination, selected appropriately from the group consisting of SEQ ID NO:11 to SEQ ID NO:16 (i.e., complementary to at least one primer used in the amplification). In all cases, the amplified nucleic acid hybridizes specifically with the appropriate probe.

We claim:

1. A combination of at least two oligonucleotides selected from the group consisting of:
   a base sequence consisting of a target-specific sequence of SEQ ID NO:3 (GCCCATTGTGCAATATTCCCCACT),
   a base sequence consisting of SEQ ID NO:3, and
   a base sequence consisting essentially of SEQ ID NO:8.

2. The combination of claim 1, further comprising at least one labeled probe oligomer.

3. A kit containing at least one oligonucleotide selected from the group consisting of
   a base sequence consisting of a target-specific sequence of SEQ ID NO:3 (GCCCATTGTGCAATATTCCCCACT),
   a base sequence consisting of SEQ ID NO::3, and
   a base sequence consisting of SEQ ID NO:8.

4. The kit of claim 1, further containing one or more labeled probe oligomers.

5. The combination of claim 1, wherein the at least two oligonucleotides are of SEQ ID NO:3 and SEQ ID NO:8.

6. The combination of claim 1, the at least two oligonucleotides are a base sequence consisting of the target-specific sequence of SEQ ID NO:3 (GCCCATTGTGCAATATTCCCCACT) and the oligonucleotide base sequence consisting of consists of SEQ ID NO:8.

7. The kit of claim 3, wherein the oligonucleotide has the base sequence consisting of the target-specific sequence of SEQ ID NO:3 (GCCCATTGTGCAATATTCCCCACT).

8. The kit of claim 3, wherein the oligonucleotide has the base sequence consisting of SEQ ID NO:8.

9. The kit of claim 3, further containing at least one unlabeled helper probe oligonucleotide.

10. The kit of claim 3, wherein the oligonucleotide has the base sequence consisting of SEQ ID NO:3.

11. The kit of claim 3, containing a combination of oligonucleotides having the base sequences consisting of SEQ ID NO:3 and SEQ ID NO:6.

12. The kit of claim 3, containing a combination of oligonucleotides having the base sequences consisting of the target-specific sequence of SEQ ID NO:3 (GCCCATTGTGCAATATTCCCCACT) and SEQ ID NO:8.

* * * * *

UNITED STATES PATENT AND TRADEMARK OFFICE
CERTIFICATE OF CORRECTION

PATENT NO. : 6,747,141 B2
DATED : June 8, 2004
INVENTOR(S) : Steven T. Brentano and Roger L. Lankford It is certified that error appears in the above-identified patent and that said Letters Patent is hereby corrected as shown below:

Column 25,
Line 32, delete "essentially".
Line 42, delete "claim 1" and insert -- claim 3 --.

Column 26,
Line 43, delete "SEQ ID NO:6" and insert instead -- SEQ ID NO:8 --.
Line 47, after "claim 1", insert "wherein" and
Line 51, delete "consists of".
Insert the following claims as allowed:

13. A method of detecting Mycobacterium avium complex (MAC) species present in a biological sample, comprising the steps of:
   providing a biological sample containing nucleic acid from at least one MAC species selected from the group consisting of M. tuberculosis, M. avium, M. intracellulare, and M. paratuberculosis, the nucleic acid comprising 16S ribosomal RNA (rRNA) or DNA encoding 16S rRNA;
   amplifying the 16S rRNA or DNA encoding 16S rRNA in an in vitro nucleic acid amplification mixture comprising at least one polymerase activity, and at least one first primer consisting of a target-specific sequence of SEQ ID NO:3 (GCCCATTGTGCAATATTCCCCACT) or the sequence of SEQ ID NO: 3, and at least one second primer consisting of the sequence of SEQ ID NO:8, to produce an amplified nucleic acid; and
   detecting the amplified nucleic acid.

14. The method of Claim 13, wherein the detecting step comprises hybridizing the amplified nucleic acid to at least one probe and detecting a signal resulting from the amplified nucleic acid that is hybridized to the probe.

15. The method of Claim 13, wherein the detecting step uses at least one labeled probe comprising sequence complementary to a portion of the amplified nucleic acid.

16. The method of Claim 13, further comprising the step of using at least one capture oligonucleotide that specifically hybridizes to nucleic acid from at least one MAC species to bind the nucleic acid from the MAC species to an immobilized nucleic acid, to purify the nucleic acid from the MAC species from other components in the sample before the amplifying step.

17. The method of Claim 13, wherein the amplifying step amplifies 16S rRNA from M. tuberculosis, M. avium, M. intracellulare, M. paratuberculosis or any combination thereof.

18. The method of Claim 13, wherein the amplifying step uses a combination of the first primer consisting of SEQ ID NO:3, and the second primer consisting of SEQ ID NO:8.

UNITED STATES PATENT AND TRADEMARK OFFICE
CERTIFICATE OF CORRECTION

PATENT NO. : 6,747,141 B2
DATED : June 8, 2004
INVENTOR(S) : Steven T. Brentano and Roger L. Lankford It is certified that error appears in the above-identified patent and that said Letters Patent is hereby corrected as shown below:

19. The method of Claim 13, wherein the amplifying step uses a combination of the first primer consisting of the target-specific sequence of SEQ ID NO:3 (GCCCATTGTGCAATATTCCCCACT) and the second primer consisting of SEQ ID NO:8.

20. The method of Claim 13, wherein the amplifying step uses transcription-mediated amplification and a combination of the first primer of SEQ ID NO:3, and the second primer consisting of SEQ ID NO:8.

Signed and Sealed this

Ninth Day of November, 2004

JON W. DUDAS
*Director of the United States Patent and Trademark Office*